United States Patent [19]

Bonzel

[11] Patent Number: 4,762,129
[45] Date of Patent: Aug. 9, 1988

[54] DILATATION CATHETER

[76] Inventor: Tassilo Bonzel, Neumattenstrasse 27, D-7800 Freiburg, Fed. Rep. of Germany

[21] Appl. No.: 893,558
[22] PCT Filed: Nov. 15, 1985
[86] PCT No.: PCT/DE85/00479
 § 371 Date: Jul. 14, 1986
 § 102(e) Date: Jul. 14, 1986
[87] PCT Pub. No.: WO86/03129
 PCT Pub. Date: Jun. 5, 1986

[30] Foreign Application Priority Data

Nov. 23, 1984 [DE] Fed. Rep. of Germany ....... 3442736

[51] Int. Cl.4 .......................................... A61M 29/02
[52] U.S. Cl. ...................................... 128/344; 604/96
[58] Field of Search .................. 128/344, 325, 348.1, 128/10, 656, 658, 772, 673, 675, 748, 207.15; 604/96–103, 281, 282

[56] References Cited

U.S. PATENT DOCUMENTS

| 1,060,665 | 5/1913 | Bell | 604/281 |
|---|---|---|---|
| 2,883,986 | 9/1957 | DeLuca et al. | 604/96 |
| 3,731,692 | 5/1973 | Goodyear | 128/207.15 |
| 3,769,981 | 11/1973 | McWhorter | 604/96 |
| 3,882,852 | 5/1975 | Sinnreich | 128/4 |
| 4,198,981 | 4/1980 | Sinnreich | 128/344 |
| 4,289,128 | 9/1981 | Rusch | 128/207.15 |
| 4,367,747 | 1/1983 | Witzel | 128/344 |
| 4,413,989 | 11/1983 | Schjeldahl et al. | 604/96 |
| 4,439,186 | 3/1984 | Kuhl | 604/99 |
| 4,545,390 | 10/1985 | Leary | 128/772 |
| 4,585,000 | 4/1986 | Hershenson | 128/345 |
| 4,616,648 | 10/1986 | Simpson | 128/303 R |
| 4,662,368 | 5/1987 | Hussein et al. | 128/303.1 |

FOREIGN PATENT DOCUMENTS

| 867144 | 12/1952 | Fed. Rep. of Germany . |
| 2828447 | 9/1979 | Fed. Rep. of Germany | 128/207.15 |
| 2918282 | 11/1980 | Fed. Rep. of Germany . |
| 3107392 | 9/1982 | Fed. Rep. of Germany . |
| 329354 | 7/1903 | France . |
| 1566308 | 4/1980 | United Kingdom . |
| 2180454 | 4/1987 | United Kingdom . |

Primary Examiner—Dalton L. Truluck
Assistant Examiner—Frank Wilkens
Attorney, Agent, or Firm—Charles J. Knuth; Peter C. Richardson; Lawrence C. Akers

[57] ABSTRACT

A dilatation catheter, in particular for expanding constrictions in coronary vessels, includes a balloon (2) capable of being enlarged by injecting a fluid through a tube (3). The tube (3) is arranged laterally offset from a segment of flexible tubing (7) by which a passage (8) for a guide wire (1) is formed in the balloon (2).

7 Claims, 1 Drawing Sheet

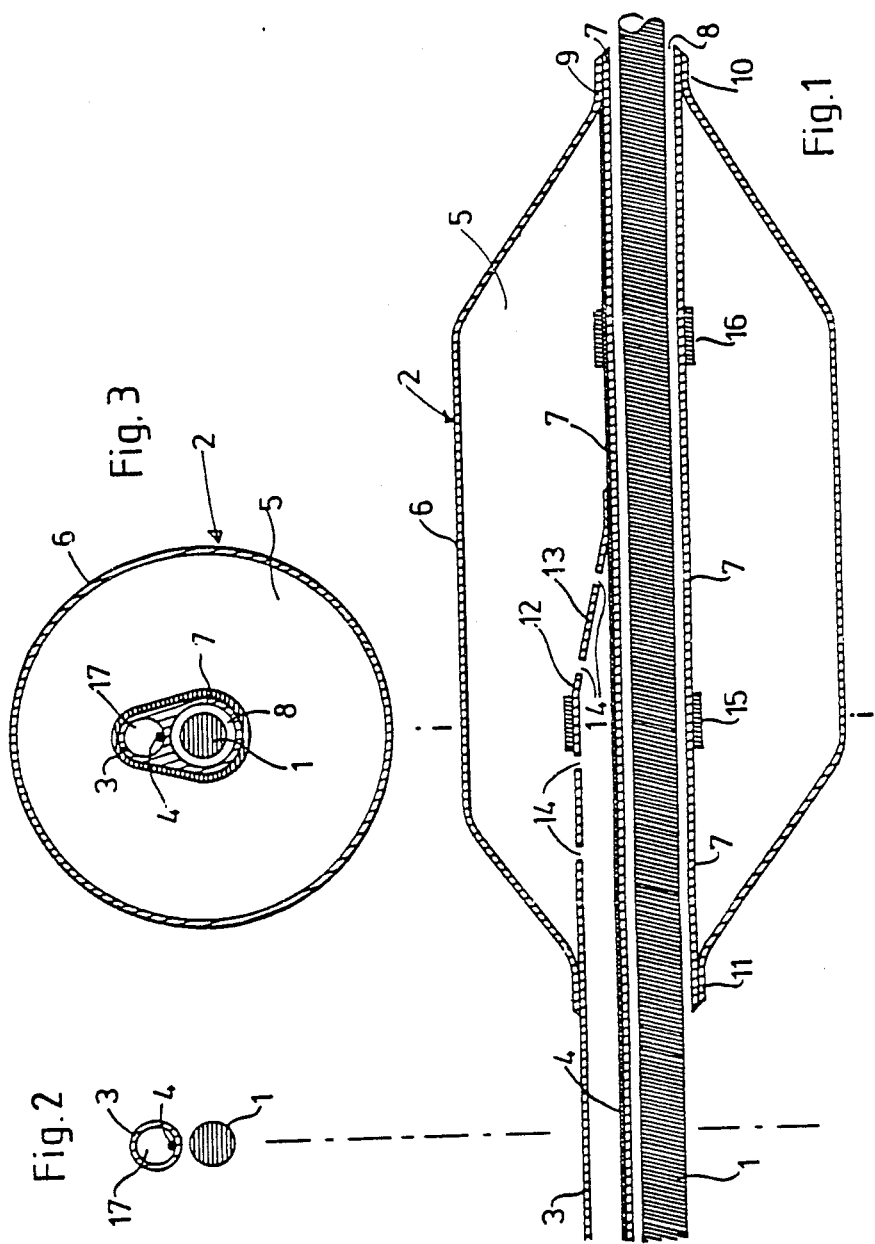

DILATATION CATHETER

BACKGROUND OF THE INVENTION

The invention relates to a dilatation catheter having a tube the operative end of which opens into an expandable balloon and a segment of flexible tubing traversing the balloon, sealingly connected to the distal end of the balloon, and capable of being threaded by a guide wire.

Such a dilatation catheter is described in The American Journal of Cardiology, Vol. 49, Apr. 1, 1982, pages 1216 to 1222, and is employed to enlarge constrictions in vessels and body cavities, in particular coronary arteries. At the tip of such a dilatation catheter, an inflatable balloon is disposed, capable of being filled or emptied by way of a lumen inside the catheter.

In the known dilatation catheter, a tube is provided that passes over into a balloon at its anterior end. Through the interior of the balloon and the tube, in the known dilatation catheter, a flexible tube extends, projecting beyond the anterior end of the balloon and sealingly connected to the anterior end of the balloon. Through the inside of the flexible tube, a guide wire is passed, capable of being displaced relative to the balloon during the operation, so that the dilatation catheter can be advanced or retracted along the guide wire. When replacing a dilatation catheter applied with the aid of a guide catheter, it is necessary that the guide wire protrude from the patient's body by a length greater than the length of the dilatation catheter with tube. For this reason, manipulation of the known dilatation catheter is difficult, especially since the forces of friction between the guide wire and the flexible tubing passing all the way through the balloon and the tube are great.

SUMMARY OF THE INVENTION

Departing from this prior art, the object of the invention is to create a dilatation catheter that can be passed easily along a guide wire and simply and easily replaced by another dilatation catheter.

This object is accomplished, according to the invention, in that the proximal end of the balloon is likewise sealingly attached to the length of flexible tubing, and in that the tube opens into the interior of the balloon laterally displaced from the segment of tubing.

Since the segment of tubing coming into contact with the surface of the guide wire is only about as long as the balloon and the tube no longer encloses the guide wire and the guide tubing enclosing it, manipulation of the dilatation catheter is facilitated. Control is improved because of the absence of frictional forces in a long segment of guide tubing. Furthermore, owing to the comparative shortness of the length of tubing, the guide wire need no longer protrude from the patient's body by about the same length as the length of the dilatation catheter.

Suitable embodiments and refinements of the invention are described elsewhere in the present application.

DETAILED DESCRIPTION OF THE INVENTION

The invention will now be illustrated with reference to the embodiment represented in the drawing by way of example. In the drawing, FIG. 1 shows the anterior portion of the dilatation catheter according to the invention, with tube opening into the balloon, FIG. 2 shows a cross section of a dilatation catheter in the region of the tube, passing alongside the guide wire, and FIG. 3 shows a cross section of the dilatation catheter in the region of a gold marker in the balloon.

In FIG. 1, the anterior portion of a dilatation catheter is represented, to be advanced with the aid of a guide catheter not shown in the drawing, having a diameter of some millimeters and a length of about one meter, for example from a patient's right groin throughout the length of the artery to the aorta and the coronary arteries. Through the guide catheter not shown in the drawing, first a guide wire 1 is advanced into the corresponding coronary. A segment of the guide wire 1, which is about 1 m in length, may be seen in FIG. 1. The guide wire 1 serves as instrumentation track to guide the dilatation catheter.

The dilatation catheter has a balloon tube and a tube 3, shown cut away in FIG. 1 and likewise on the order of 1 m in length.

FIG. 2 shows a section of the guide wire 1 and tube 3. The tube 3 serves firstly to transmit thrusts and tensions for pushing the balloon 2 to and fro and rotating it on the guide wire 1. For this reason, it is desirable for the tube 3 to be reinforced by a stabilizing wire 4 in the manner shown in FIGS. 1 to 3. Besides its function of transmitting forces, the tube 3 serves for injection of fluids into the interior 5 of the balloon 2 and for aspiration of fluids when the diameter of the balloon is to be decreased.

As may be seen in FIG. 1, the balloon consists of an envelope 6 and a length of flexible tubing 7, so that the balloon 2 has a passage 8 sealed off from the interior 5 of the balloon. The balloon passage 8 enables the balloon 2 to be thrust onto the guide wire 1 and thereby guided along the guide wire 1.

In FIG. 3, the substantially annular cross section of the balloon 2 is seen, together with the balloon passage 8 through which the guide wire 1 extends. For good transmission of the forces exerted upon the tube 3 to the balloon 2, the stabilizing wire 4 extends into the neighborhood of the distal end 9 of the balloon 2.

As is clearly seen in FIG. 1, at the distal end 9 of the balloon 2 the envelope 6 takes the form of a length of flexible tubing 10, tightly connected to the distal end of the segment of tubing 7. Similarly, the envelope 6 terminates at the proximal end in a segment of tubing 11, sealingly connected firstly to the proximal end of segment 7 and secondly to the tube 3.

The operative end 12 of tube 3, pointing to the right in FIG. 1, terminates in a taper 13 fixed to the tubing 7. Both in the taper 13 and elsewhere at the operative end 12, radial openings 14 are provided in the tube 3, whereby fluid injected into the tube 3 can pass from the tube 3 into the interior 5 of the balloon 2.

In FIGS. 1 and 3, gold stripes 15 and 16 are additionally represented, serving to mark the location of the dilatation catheter in X-ray views.

In FIG. 3, we see a cross section of the balloon 2 in the region of the gold strip 15. The tube 3 with its inner lumen 17 and the segment of tubing 7 with balloon passage 8 are made in one piece in the region shown in FIG. 3, so that the gold stripe 15 assumes a substantially oval form rather than that of a figure-eight.

The guide wire 1 may have a central lumen, not shown in the drawing, for pressure measurement or to contain a contrast medium. To minimize frictional resistance between the interior of the balloon passage 8 and the surface of the guide wire 1, the inside of the tubing segment 7, reinforced by the stabilizing wire 4, and/or the top of the guide wire 1 may be provided with a lubricant coating.

For dilatation of coronary vessels, first the guide wire 1 is introduced through the guide catheter into the proper coronary artery. The guide wire 1 lies freely in the guide catheter and so may be conveniently rotated and controlled. For anatomical orientation, adequate additional doses of contrast medium may be supplied. When the guide wire 1 has passed the constriction in the coronary artery, the tip of the guide wire 1 remains on the far side of the stenosis in the coronary vessel. At this point, and not until, the dilatation catheter according to the invention is thrust onto the guide wire 1 outside the body and advanced through the guide catheter along the track formed by the guide wire 1 into the coronary artery and under the constriction. If the balloon 2 is to be replaced during the operation by a balloon 2 of larger size, it is a simple matter to retract the dilatation catheter according to the invention, leaving the anterior end of the guide wire 1 in the coronary vessel and permitting secure advancement of the replacement balloon with no need to overcome much friction or to relocate the stenosis a second time. If deficient stability of the result of dilatation is suspected, the guide wire 1 may even be left in place for several hours, with a view to renewed dilatation at a later time. The distal end 9 of the dilatation catheter is flattened in the manner described above for better insertability into vascular constrictions.

The invention permits the provision of balloons of various lengths, widths and wall thicknesses to accommodate various pressures, and they may be interchanged with ease. Depending on medical requirements, the dilatation catheters are equipped with tubes 3 of varying weight and flexibility, admitting of differential advance. For larger dilatation catheters, an additional inner lumen, not shown in the drawing, is provided, its anterior end extending to the distal end 9 of the balloon 2 and communicating with the interior of the vessel inside the patient's body. In this way, pressure measurements and injections of contrast medium may be performed. The guide wires 1 of a complete instrumentarium are likewise of different weights and flexibilities. The guide wires 1 have soft, flexible tips, which may be shorter or longer, as well as straight or bowed. If no additional inner lumen is provided in the balloon, a central lumen as above mentioned may be provided in the guide wires for pressure measurements and injections of contrast medium.

I claim:

1. A dilatation catheter comprising an expandable balloon having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends and a lumen extending between said ends of uniform cross section along its length and free of obstructions adapted to receive a guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube, in combination with an elongated guide wire.

2. The combination of claim 1 wherein the guide wire is provided with a central lumen for pressure measurement and/or injection of contrast medium.

3. The combination of claim 1 wherein the first tube is reinforced by means of a longitudinally-extending stabilizing means.

4. A dilatation catheter comprising an expandable balloon having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends, and adapted to receive a guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube, in combination with an elongated guide wire.

5. A method for opening a constricted region in the vascular system of a patient comprising the steps of:

(a) providing an elongated guide wire and a dilatation catheter comprising an expandable balloon having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends, and adapted to receive said guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube;

(b) inserting said guide wire into the vascular system of the patient;

(c) positioning said catheter so that said guide wire is in a sliding fit within said second elongated hollow tube;

(d) advancing said catheter along said guide wire into and within said vascular system, with said expandable balloon in an unexpanded condition, until said expandable balloon is situated within said constricted region;

(e) expanding the expandable balloon to open the constricted region;

(f) contracting the expandable balloon; and (g) withdrawing said catheter and said guide wire from the body of the patient.

6. A method for opening a constricted region in the vascular system of a patient comprising the steps of:

(a) providing an elongated guide wire and a dilatation catheter comprising an expandable balloon having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends and a lumen extending between said ends of uniform cross section along its length and free of obstructions adapted to receive a guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube, with said second elongated hollow tube being adapted to receive said guide wire in a sliding fit;

(b) inserting said guide wire into the vascular system of the patient;

(c) positioning said catheter so that said guide wire is in a sliding fit within said second elongated hollow tube;

(d) advancing said catheter along said guide wire into and within said vascular system, with said expandable balloon in an unexpanded condition, until said expandable balloon is situated within said constricted region;

(e) expanding the expandable balloon to open the constricted region;

(f) contracting the expandable balloon; and (g) withdrawing said catheter and said guide wire from the body of the patient.

7. A method of claim 6 wherein the first tube is reinforced by means of a longitudinally-extending stabilizing means.

* * * * *

UNITED STATES PATENT AND TRADEMARK OFFICE
CERTIFICATE OF CORRECTION

PATENT NO. : 4,762,129
DATED : August 9, 1988
INVENTOR(S) : Tassilo Bonzel

It is certified that error appears in the above-identified patent and that said Letters Patent is hereby corrected as shown below:

Change column 4, lines 10 and 11, from

"    upon the first tube, in combination with an elongated guide wire."    to

--    upon the first tube, in combination with an elongated guide wire.--

Signed and Sealed this

Twenty-ninth Day of November, 1988

*Attest:*

DONALD J. QUIGG

*Attesting Officer*    *Commissioner of Patents and Trademarks*

UNITED STATES PATENT AND TRADEMARK OFFICE
CERTIFICATE OF CORRECTION

PATENT NO. : 4,762,129
DATED : 8/9/88
INVENTOR(S) : Tassilo Bonzel

It is certified that error appears in the above-identified patent and that said Letters Patent is hereby corrected as shown below:

On the title page

Item [76] should read  Inventor:  Tassilo Bonzel
Monnetstrasse 14
D-36039 Fulda
Germany Signed and Sealed this Twelfth Day of May, 1998

*Attest:*

BRUCE LEHMAN

*Attesting Officer*      Commissioner of Patents and Trademarks

REEXAMINATION CERTIFICATE (1501st)

United States Patent [19]

Bonzel

[11] B1 4,762,129

[45] Certificate Issued Jul. 2, 1991

[54] DILATATION CATHETER

[76] Inventor: Tassilo Bonzel, Neumattenstrasse 27, D-7800 Freiburg, Fed. Rep. of Germany

Reexamination Request
No. 90/001,647, Nov. 25, 1988
No. 90/001,870, Oct. 25, 1989
No. 90/001,965, Mar. 16, 1990
No. 90/002,016, May 4, 1990

Reexamination Certificate for:
| | |
|---|---|
| Patent No.: | 4,762,129 |
| Issued: | Aug. 9, 1988 |
| Appl. No.: | 893,558 |
| Filed: | Nov. 15, 1985 |

[22] PCT Filed: Nov. 15, 1985

[86] PCT No.: PCT/DE85/00479

§ 371 Date: Jul. 14, 1986

§ 102(e) Date: Jul. 14, 1986

[87] PCT Pub. No.: WO86/03129

PCT Pub. Date: Jun. 5, 1986

[30] Foreign Application Priority Data

Nov. 23, 1984 [DE] Fed. Rep. of Germany ....... 3442736

[51] Int. Cl.$^5$ ............................................. A61M 29/02
[52] U.S. Cl. ..................................... 606/194; 604/96
[58] Field of Search ................................. 604/96–103; 606/127, 159, 194, 200

[56] References Cited

U.S. PATENT DOCUMENTS

| | | |
|---|---|---|
| 1,060,665 | 5/1913 | Bell . |
| 2,383,986 | 9/1957 | DeLuca et al. . |
| 2,657,691 | 11/1953 | Nordstrom, Jr. . |
| 2,687,131 | 8/1954 | Raiche . |
| 2,936,760 | 5/1960 | Gants . |
| 3,225,762 | 12/1965 | Guttmann . |
| 3,435,826 | 4/1969 | Fogarty et al. . |
| 3,467,101 | 9/1969 | Fogarty et al. . |
| 3,731,692 | 5/1973 | Goodyear . |
| 3,757,768 | 9/1973 | Kline . |
| 3,766,924 | 10/1973 | Pidgeon . |
| 3,769,981 | 11/1973 | McWhorter . |
| 3,882,852 | 5/1975 | Sinnreich . |
| 4,195,637 | 4/1980 | Gruntzig et al. . |
| 4,198,981 | 4/1980 | Sinnreich . |
| 4,236,521 | 12/1980 | Lauterjung . |
| 4,244,362 | 1/1981 | Anderson . |
| 4,271,839 | 6/1981 | Fogarty et al. ........................ 128/344 |
| 4,289,128 | 9/1981 | Rusch . |
| 4,299,226 | 11/1981 | Banka . |
| 4,323,071 | 4/1982 | Simpson et al. . |
| 4,367,747 | 1/1983 | Witzel . |
| 4,413,989 | 11/1983 | Schjeldahl et al. . |
| 4,439,186 | 3/1984 | Kuhl . |
| 4,468,224 | 8/1984 | Enzmann et al. .................... 128/348 |
| 4,479,497 | 10/1984 | Fogarty et al. . |
| 4,490,421 | 12/1984 | Levy . |
| 4,526,175 | 7/1985 | Chin et al. ........................... 128/344 |
| 4,545,390 | 10/1985 | Leary . |
| 4,554,929 | 11/1985 | Samson et al. ...................... 128/772 |
| 4,571,240 | 2/1986 | Samson et al. . |
| 4,573,966 | 3/1986 | Weikl et al. . |
| 4,582,181 | 4/1986 | Samson . |
| 4,585,000 | 4/1986 | Horshenson . |
| 4,597,755 | 7/1986 | Samson et al. . |
| 4,610,662 | 9/1986 | Weikl et al. ........................... 604/43 |
| 4,616,648 | 10/1986 | Simpson ............................. 128/303 |
| 4,630,609 | 12/1986 | Chin . |
| 4,637,396 | 1/1987 | Cook . |
| 4,662,368 | 5/1987 | Hussein et al. . |
| 4,684,363 | 8/1987 | Ari et al. . |
| 4,702,252 | 10/1987 | Brooks et al. . |
| 4,824,435 | 4/1989 | Giesy et al. . |

FOREIGN PATENT DOCUMENTS

| | | |
|---|---|---|
| 867144 | 12/1952 | Fed. Rep. of Germany . |
| 2828447 | 9/1979 | Fed. Rep. of Germany . |
| 2918282 | 11/1980 | Fed. Rep. of Germany . |
| 3028089 | 2/1981 | Fed. Rep. of Germany . |
| 2934628 | 3/1981 | Fed. Rep. of Germany . |
| 3107392 | 9/1982 | Fed. Rep. of Germany . |
| 329354 | 7/1903 | France . |
| 591963 | 7/1925 | France . |
| 627828 | 10/1978 | U.S.S.R. . |
| 1251914 | 8/1986 | U.S.S.R. . |
| 1566308 | 4/1980 | United Kingdom . |
| 2180454 | 4/1987 | United Kingdom . |

OTHER PUBLICATIONS

Kinney et al., "Transluminal Angioplasty: A Mechanical-Pathophysiological Correlation Of Its Physical Mechanisms", *Radiology*, vol. 153, pp. 85–89 (Oct. 1984).

Earlam et al., "Benign Oesophagael Strictures: Historical And Technical Aspects of Dilatation", *The British Journal of Surgery*, vol. 68, No. 12, pp. 828–836 (Dec. 1981).

Portsmann, "Ein Neuer Korsett-Ballonkatheter Zur Transluminalen Rekanalisation Nach Dotter Unter Besonderer Berucksichtigung Von Obliterationen An Den Beckenarterien", *Radio. Diagn.* (Berl), vol. 14, pp. 239–244 (1973).

Fogarty and Finn, "Peroperative Transluminal Angioplasty", pp. 313–321.

Taber's Cyclopedic Medical Dictionary p. 768.

The Condensed Chemical Dictionary revised by Gessner G. Hawley p. 836 (1981).

Nordenstrom, "Balloon Catheters for Percutaneous Insertion into the Vascular System", *Acta Radiology*, vol. 57, pp. 411–416 (Nov. 1962).

Nordenstrom, "Temporary Unilateral Occlusion of the Pulmonary Artery: A Method of Roetgen Examination of the Pulmonary Vessels", *Acta Radiology Suppl.*, No. 108, pp. 1–30 (1954).

Simpson et al., "A New Catheter System for Coronary Angioplasty", *Am. Jour. Cardiology*, 49: 1216–1222 (Apr. 1982).

Dotter, C. T., "Transluminal Angioplasty: A Long View", *Radiology*, 135:561–564 (Jun. 1980).

Zeitler et al., "Results of Percutaneous Transluminal Angioplasty", *Radiology*, 146: 57–60 (Jan. 1983).

Hawkins et al., "Minicatheter and Deflector Technique for Renal Angioplasty", *Radiology*, 145: 837–838 (Dec. 1982).

Nordenstrom, B., "New Instruments for Catherization and Angiocardiography", *Radiology*, vol. 85, pp. 256–259 (Jul.-Dec. 1965).

Fogarty et al., "A Method for Extraction of Arterial Emboli and Thrombi", *Surgery, Gynecology & Obstetrics*, pp. 241–243 (Feb. 1963).

Fogarty et al., "Adjunctive Intraoperative Arterial Dilation", *Arch. Surg.*, vol. 116, pp. 1391–1397 (Nov. 1981).

Gruntzig, "PTCA Technique With A Double Lumen Dilatation Catheter" published in *Proceeding of the Workshop on Percutaneous Transluminal Coronary Angioplasty*, NIH Publication No. 80-2030, pp. 123–133 (Mar. 1980).

McAuley et al., "Advances in Guidewire Technology", *Am. J. Cardiol.*, 53:94C–96C (1984).

21 C.F.R. §§870.1–870.1650 (1980).

Fogarty Arterial Embolectomy Catheter Instructors, American Edwards Laboratories, pp. 1–4 (Aug. 1984).

Fogarty, "Management of Arterial Emboli", *Surgical Clinics of N. America*, vol. 59, No. 4, pp. 747–753 (Aug. 79).

Fogarty et al., "Combined Thrombectomy and Dilation for the Treatment of Acute Lower Extremity Arterial Thrombosis", *J. Vasc. Surg.*, vol. 10, No. 5, pp. 530–534 (Nov. 1989).

Fogarty et al., "Intraoperative Coronary Artery Balloon-Catheter Dilatation", *Am. Heart J.*, vol. 107, No. 9, pp. 845–851 (Apr. 1984).

Abele, "Balloon Catheters and Transluminal Dilatation: Technical Considerations", *AJR*, vol. 135, pp. 901–906 (Nov. 1980).

Waltman et al., "Transluminal Angioplasty: General Rules and Basic Considerations", in *Interventional Radiology*, pp. 253–272 (1982).

Castaneda-Zuniga, *Transluminal Angioplasty*, pp. 1–27 (1983).

Gruntzig et al., "Current Status of Dilatation Catheters and Guiding Systems", *Am. J. Cardiol.*, vol. 53, pp. 92C–93C (Jun. 1984).

Kaltenbach, "The Long Wire Technique—A New Technique for Steerable Balloon Catheter Dilatation of Coronary Artery Stenosis", *European Heart J.*, vol. 5, pp. 1004–1009 (Dec. 1984).

Kaltenbach, "Neue Technik Zur Steuerbaren Ballondilatation VonKranzgefaRverongungen", *Z. Kardiol.*, 73: 669–673 (Nov. 1984).

Seldinger, "Catheter Replacement of the Needle in Percutaneous Arteriography", *Acta Radiol.*, vol. 39, pp. 368–376 (1952).

Nordenstrom, "Percutaneous Balloon-Occlusion of the Aorta", *Acta Radiol.*, vol. 4, pp. 356–374 (1966).

Friedberg, "Dilatation of Esophagael Strictures in Children, Using A Fogarty Balloon Catheter" presented at 33rd Annual Meeting of Canadian Othotaryngological Society (Jun. 1979).

Kuyimija et al., "The Use of a Fogarty Balloon Catheter for Dilatation of Postoperative Esophagael Stricture", *Kyobu Geka*, vol. 30, No. 5, pp. 419–422 (1977).

Gruntzig, "Transluminal Dilatation of Coronary Stenosis", *Lancet* 1:263 (1978).

Annual Review of Medicine: Selected Topics in the Clinical Sciences, Kennedy & Stewart, vol. 35, pp. 514–522 (1984).

Cumberland, "Percutaneous Transluminal Angioplasty: A Review", *Clinical Radiology*, vol. 34, pp. 25–38 (1983).

Moersch, "Cardiospasm: Its Diagnosis and Treatment", pp. 232–238 (1932).

*Primary Examiner*—Michael H. Thaler

[57] ABSTRACT

A dilatation catheter, in particular for expanding constrictions in coronary vessels, includes a balloon (2) capable of being enlarged by injecting a fluid through a tube (3). The tube (3) is arranged laterally offset from a segment of flexible tubing (7) by which a passage (8) for a guide wire (1) is formed in the balloon (2).

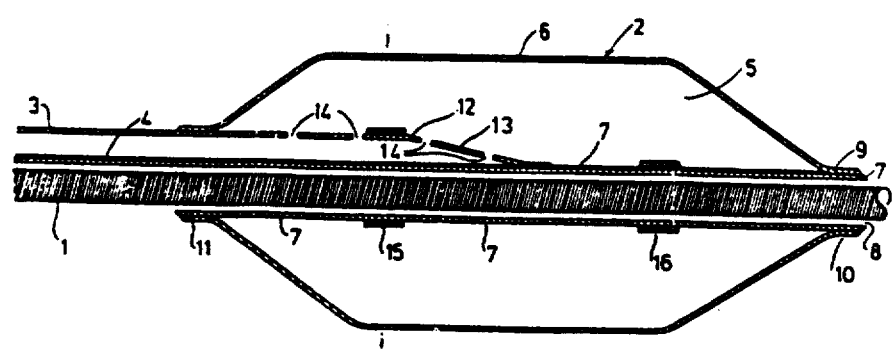

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1 and 3–7 are determined to be patentable as amended.

New claims 8–27 are added and determined to be patentable.

1. A dilatation catheter comprising an expandable balloon having distal and proximal ends, *wherein the balloon is elongated in the longitudinal direction of the dilatation catheter and exhibits, upon expansion, a substantially cylindrical central working portion between said distal and proximal ends*, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends and a lumen extending between said ends of uniform cross section along its *entire* length and free of obstructions adapted to receive a guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube, [in combination with an elongated guide wire]
*in combination with an elongated guide wire received in a sliding fit within said second hollow tube,*
  *said guide wire having a proximal portion and a distal portion with a flexible tip, and having sufficient stiffness that it can readily be advanced in use distally through a body lumen by exerting a pushing force upon its proximal portion, with the proximal end of said elongated guide wire adapted to be readily slid into and out of the distal end of said second hollow tube during a dilatation procedure.*

3. The combination of claim [1] *8* wherein the first *hollow* tube is reinforced by means of [a] *an integral non-removable* longitudinally-extending stabilizing means.

4. A dilatation catheter comprising an expandable balloon having distal and proximal ends, *wherein the balloon is elongated in the longitudinal direction of the dilatation catheter and exhibits, upon expansion, a substantially cylindrical central working portion between said distal and proximal ends*, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends, and adapted to receive a guide wire in a sliding fit, the second tube traversing the interior of the expandable balloon from the distal end to the proximal end of the balloon and being sealingly connected to the distal end of the balloon, *and wherein the shortest distance between the substantially cylindrical working surface of the balloon upon expansion and the outer surface of the second elongated hollow tube is substantially greater than the width in cross-section of the second elongated hollow tube*, and the second tube terminating at its proximal end substantially distally of the proximal end of the first tube in an aperture open to the exterior of the catheter,
  said first tube having sufficient stiffness that the second tube and expandable balloon can readily be advanced or withdrawn together in use along the guide wire by exerting a pushing or pulling force upon the first tube,
in combination with an elongated guide wire *received in a sliding fit within said second hollow tube,*
  *said guide wire having a proximal portion and a distal portion with a flexible tip, and having sufficient stiffness that it can readily be advanced in use distally through a body lumen by exerting a pushing force upon its proximal portion, with the proximal end of said elongated guide wire adapted to be readily slid into and out of the distal end of said second hollow tube during a dilatation procedure.*

5. A method for opening a [constricted region] *constriction* in the vascular system of a patient comprising the steps of:
  (a) providing an elongated guide wire *having distal and proximal ends* and a dilatation catheter comprising an expandable balloon having distal and proximal ends, a first, relatively long, elongated hollow tube having distal and proximal ends and opening adjacent its distal end into interior of the expandable balloon, the first tube being sealingly connected to the proximal end of the balloon, and a second, relatively short, elongated hollow tube integral with said first tube, having distal and proximal ends, and adapted to receive said guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube;
  (b) inserting said guide wire into the vascular system of the patient;
  (c) *then* positioning said catheter *over the proximal end of said guide wire* so that said guide wire is in a sliding fit within said second elongated hollow tube;

(d) advancing said catheter along said guide wire into and within said vascular system, with said expandable balloon in an unexpanded condition, until said expandable balloon is situated within said [constricted region] *constriction;*

(e) expanding the expandable balloon *situated within said constriction* to open the [constricted region] *constriction during the expansion of the balloon by the compressive force of the expanding balloon against said constriction;*

(f) contracting the expandable balloon *while within the site of the opened constriction, said site remaining opened after the expandable balloon is contracted;* and *thereafter*

(g) withdrawing said catheter and said guide wire from the body of the patient.

6. A method for opening a [constricted region] *constriction* in the vascular system of a patient comprising the steps of:

(a) providing an elongated guide wire *having distal and proximal ends* and a dilatation catheter comprising an expandable balloon having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends and a lumen extending between said ends of uniform cross section along its length and free of obstructions adapted to receive a guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube, with said second elongated hollow tube being adapted to receive said guide wire in a sliding fit;

(b) inserting said guide wire into the vascular system of the patient;

(c) *then* positioning said catheter *over the proximal end of said guide wire* so that said guide wire is in a sliding fit within said second elongated hollow tube;

(d) advancing said catheter along said guide wire into and within said vascular system, with said expandable balloon in an unexpanded condition, until said expandable balloon is situated within said [constricted region] *constriction;*

(e) expanding the expandable balloon *situated within said constriction* to open the [constricted region] *constriction during the expansion of the balloon by the compressive force of the expanding balloon against said constriction;*

(f) contracting the expandable balloon *while within the site of the opened constriction, said site remaining opened after the expandable balloon is contracted;* and *thereafter*

(g) withdrawing said catheter and said guide wire from the body of the patient.

7. [A] *The* method of claim 6 wherein the first tube is reinforced by means of a longitudinally-extending stabilizing means.

8. The combination of claim 4 wherein said elongated guide wire is a steerable guide wire.

9. *The method of claim 5 wherein the expandable balloon is elongated in the longitudinal direction of the dilatation catheter and exhibits, upon expansion, a substantially cylindrical central working portion between the distal and proximal ends of said balloon.*

10. *The method of claim 5 wherein the first hollow tube is reinforced by means of an integral non-removable longitudinally-extending stabilizing means.*

11. *A coronary angioplasty dilatation catheter adapted for use in a coronary angioplasty procedure and dimensioned and configured for opening a constriction in a coronary artery, comprising an expandable balloon of a suitable material for opening said constriction by the exertion of compressive force when the balloon is expanded within said constriction during a coronary angioplasty procedure having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends, and adapted to receive a coronary angioplasty guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter,*

*said first tube having sufficient stiffness that the second tube and expandable balloon can readily be advanced or withdrawn together in use along the guide wire by exerting a pushing or pulling force upon the first tube,*

*in combination with an elongated coronary angioplasty guide wire received in a sliding fit within said second hollow tube,*

*said guide wire having a proximal portion and a distal portion with a flexible tip, and said guide wire adapted to be advanced during a coronary angioplasty procedure, by the manipulation of a portion of said guide wire extending from the body of a patient in the region of the groin, through the arterial system including the aorta into said coronary artery and across said constriction so that the distal tip of said guide wire is disposed on the far side of said constriction, and further adapted to guide said coronary angioplasty dilatation catheter through said arterial system into said coronary artery, and with the proximal end of said guide wire adapted to be readily slid into and out of the distal end of said second hollow tube during a coronary angioplasty procedure.*

12. *The combination of claim 11 wherein said coronary angioplasty guide wire has a solid, non-hollow cross-section in at least one transverse plane taken through said guide wire at a location displaced from the distal tip of said guide wire.*

13. *The combination of claim 11 wherein the expandable balloon is elongated in the longitudinal direction of the dilatation catheter and exhibits, upon expansion, a substantially cylindrical central working portion between said distal and proximal ends of said balloon.*

14. The combination of claim 11 wherein said dilatation catheter is about one meter in length.

15. The combination of claim 11 wherein said coronary angioplasty guide wire has a flexible, bowed distal tip.

16. The combination of claim 11 wherein said second tube has a lumen extending between said distal and proximal ends of said second tube of uniform cross section along its entire length and free of obstructions.

17. A method for opening a constriction in the vascular system of a patient, including the operation of readily exchanging dilatation catheters, comprising the steps of:

(a) providing an elongated guide wire having distal and proximal ends and a first dilatation catheter comprising an expandable balloon having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends, and adapted to receive said guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube;

(b) inserting said guide wire and said first dilatation catheter into the vascular system of the patient so that the distal tip of said guide wire has passed to the far side of the constriction and the length of the guide wire protruding from the body of the patient is less than the full length of the dilatation catheter, and said guide wire is in a sliding fit within said second elongated hollow tube;

(c) withdrawing said first dilatation catheter from the body of the patient while maintaining said guide wire in said vascular system with its distal tip on the far side of said constriction;

(d) then positioning a second dilatation catheter as described in step (a) over the proximal end of said guide wire so that said guide wire is in a sliding fit within the second elongated hollow tube of said second dilatation catheter;

(e) advancing said second dilatation catheter along said guide wire into and within said vascular system, with its expandable balloon in an unexpanded condition, until said expandable balloon is situated within said constriction;

(f) expanding the expandable balloon situated within said constriction to open the constriction during the expansion of the balloon by the compressive force of the expanding balloon against said constriction;

(g) contracting the expandable balloon while within the site of the opened constriction, said site remaining opened after the expandable balloon is contracted; and thereafter (h) withdrawing said second dilatation catheter and said guide wire from the body of the patient.

18. The method of claim 17 wherein the expandable balloon of said second dilatation catheter is different in size from the expandable balloon of said first dilatation catheter.

19. The method of claim 18 wherein the expandable balloon of said second dilatation catheter is larger in size than the expandable balloon of said first dilatation catheter.

20. The method of claim 17 wherein said vascular system is the arterial system and said constriction is in a coronary artery, wherein said first and second dilatation catheters are coronary angioplasty dilatation catheters, and wherein said guide wire is a coronary angioplasty guide wire.

21. The method of claim 20 wherein in said step (b) said coronary angioplasty guide wire is inserted into said arterial system in the region of the groin through a guiding catheter and wherein said first coronary angioplasty dilatation catheter is advanced along said guide wire through said arterial system through said guiding catheter.

22. A coronary angioplasty dilatation method for opening a constriction in a coronary artery of a patient comprising the steps of:

(a) providing an elongated coronary angioplasty guide wire having distal and proximal ends and a coronary angioplasty dilatation catheter comprising an expandable balloon having distal and proximal ends, wherein the balloon is elongated in the longitudinal direction of the dilatation catheter and exhibits, upon expansion, a substantially cylindrical central working portion between said distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends, and adapted to receive said guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube;

(b) inserting said guide wire into the arterial system of the patient and advancing said guide wire, by the manipulation of a portion of said guide wire extending from the body of the patient, through said arterial system, including the aorta, into said coronary artery and across said constriction so that the distal tip of said guide wire is disposed on the far side of said constriction;

(c) then positioning said catheter over the proximal end of said guide wire so that said guide wire is in a sliding fit within said second elongated hollow tube;

(d) advancing said catheter along said guide wire into and within said vascular system, with said expandable balloon in an unexpanded condition, until said expandable balloon is situated within said constriction;

(e) expanding the expandable balloon situated within said constriction to open the constriction during the expansion of the balloon by the compressive force of the expanding balloon against said constriction;

(f) contracting the expandable balloon while within the site of the opened constriction, said site remaining opened after the expandable balloon is contracted; and thereafter (g) withdrawing said catheter and said guide wire from the body of the patient.

23. The method of claim 22 wherein in said step (b) said coronary angioplasty guide wire is inserted into said arterial system through a guiding catheter and wherein said dilatation catheter is advanced along said guide wire through said arterial system through said guiding catheter.

24. The method of claim 22 wherein said elongated coronary angioplasty guide wire provided in step (a) has a solid, non-hollow cross-section in at least one transverse plane taken through said guide wire at a location displaced from the distal tip of said guide wire.

25. The method of claim 22 wherein in said step (b) said guide wire is inserted into the arterial system in the region of the groin and is advanced therefrom through said arterial system into said coronary artery.

26. The method of claim 25 wherein in said step (b) said coronary angioplasty guide wire is inserted into said arterial system through a guiding catheter and wherein in said step (d) said coronary angioplasty dilatation catheter is advanced along said guide wire through said arterial system through said guiding catheter.

27. A coronary angioplasty dilatation catheter adapted for use in a coronary angioplasty procedure and dimensioned and configured for opening a constriction in a coronary artery, comprising an expandable balloon of a suitable material for opening said constriction by the exertion of compressive force when the balloon is expanded within said constriction during a coronary angioplasty procedure having distal and proximal ends, a first, relatively long, elongated hollow tube having distal and proximal ends and opening adjacent its distal end into the interior of the expandable balloon, the first tube being sealingly connected to the proximal end of the balloon, and a second, relatively short, elongated hollow tube integral with said first tube, having distal and proximal ends, and adapted to receive a coronary angioplasty guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter, said first tube having sufficient stiffness that the second tube and expandable balloon can readily be advanced or withdrawn together in use along the guide wire by exerting a pushing or pulling force upon the first tube, in combination with an elongated coronary angioplasty guide wire received in a sliding fit within said second hollow tube, said guide wire having a proximal portion and a distal portion with a flexible tip, and said guide wire adapted to be advanced during a coronary angioplasty procedure, by the manipulation of a portion of said guide wire extending from the body of a patient, through the arterial system including the aorta into said coronary artery and across said constriction so that the distal tip of said guide wire is disposed on the far side of said constriction, and further adapted to guide said coronary angioplasty dilatation catheter through said arterial system into said coronary artery, and with the proximal end of said guide wire adapted to be readily slid into and out of the distal end of said second hollow tube during a coronary angioplasty procedure.

* * * * *